United States Patent
Miyahara et al.

(10) Patent No.: US 10,750,941 B2
(45) Date of Patent: Aug. 25, 2020

(54) OPTICAL MODULE, IMAGE PICKUP MODULE, AND ENDOSCOPE

(71) Applicant: OLYMPUS CORPORATION, Tokyo (JP)

(72) Inventors: Hideharu Miyahara, Nagano (JP); Youhei Sakai, Ina (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/406,433

(22) Filed: May 8, 2019

(65) Prior Publication Data
US 2019/0261842 A1  Aug. 29, 2019

Related U.S. Application Data

(63) Continuation of application No. PCT/JP2016/084071, filed on Nov. 17, 2016.

(51) Int. Cl.
*A61B 1/05* (2006.01)
*G02B 6/42* (2006.01)
(Continued)

(52) U.S. Cl.
CPC ............... *A61B 1/051* (2013.01); *G02B 6/42* (2013.01); *H01L 25/065* (2013.01); *H01L 25/18* (2013.01);
(Continued)

(58) Field of Classification Search
CPC .......... A61B 1/051; G02B 6/42; G02B 6/423; G02B 6/4239; G02B 6/4242;
(Continued)

(56) References Cited

U.S. PATENT DOCUMENTS 5,220,198 A    6/1993  Tsuji
2007/0060984 A1*  3/2007  Webb ................... A61N 5/0601
                                                    607/89
(Continued)

FOREIGN PATENT DOCUMENTS

EP          2947486 A1    11/2015
JP        H04-218136 A     8/1992
(Continued)

OTHER PUBLICATIONS

International Search Report dated Feb. 28, 2017 issued in PCT/JP2016/084071.

*Primary Examiner* — James T Boylan
(74) *Attorney, Agent, or Firm* — Scully, Scott, Murphy & Presser, P.C.

(57) ABSTRACT

An optical module includes an optical element, a first substrate, on a first principal plane of which the optical element is mounted, a holding member disposed on a second principal plane of the first substrate, an optical fiber inserted into a through hole of the holding member, a holding substrate with an opening, a wall surface of which is in contact with an outer peripheral surface of the holding member, an interconnecting substrate connecting the first substrate and the holding substrate, a side surface substrate, an end portion of which is connected to the holding substrate and on which an electrode is disposed, and a signal cable, a distal end portion of which is bonded to the electrode of the side surface substrate.

13 Claims, 15 Drawing Sheets

(51) Int. Cl.
*H01L 25/065* (2006.01)
*H01L 25/18* (2006.01)
*H01L 27/14* (2006.01)
*H04N 5/369* (2011.01)
*H04N 7/18* (2006.01)
*H01L 25/07* (2006.01)
*H04N 5/225* (2006.01)

(52) U.S. Cl.
CPC .............. *H01L 27/14* (2013.01); *H04N 5/369* (2013.01); *H04N 7/18* (2013.01); *H01L 25/07* (2013.01); *H04N 5/225* (2013.01)

(58) Field of Classification Search
CPC ....... H01L 25/065; H01L 25/07; H01L 25/18; H01L 27/14; H04N 2005/2255; H04N 5/225; H04N 5/369; H04N 7/18
USPC .......................................................... 348/82
See application file for complete search history.

(56) References Cited

U.S. PATENT DOCUMENTS

| | | | |
|---|---|---|---|
| 2014/0309495 A1* | 10/2014 | Kirma | G02B 23/243 600/109 |
| 2015/0086162 A1* | 3/2015 | Miyahara | G02B 23/2423 385/33 |
| 2015/0318924 A1* | 11/2015 | Motohara | G02B 6/4259 398/200 |

FOREIGN PATENT DOCUMENTS

| | | |
|---|---|---|
| JP | H05-049602 A | 3/1993 |
| JP | 2008-118568 A | 5/2008 |
| JP | 2014-137584 A | 7/2014 |
| JP | 2015-068835 A | 4/2015 |
| WO | WO 2014/112461 A1 | 7/2014 |

* cited by examiner

OPTICAL MODULE, IMAGE PICKUP MODULE, AND ENDOSCOPE

CROSS REFERENCE TO RELATED APPLICATION

This application is a continuation application of PCT/JP2016/084071 filed on Nov. 17, 2016, the entire contents of which are incorporated herein by this reference.

BACKGROUND OF THE INVENTION

1. Field of the Invention

The present invention relates to an optical module including an optical element configured to transmit or receive an optical signal, an optical fiber for transmitting the optical signal, a holding member configured to hold the optical fiber, and a signal cable for transmitting an electric signal, an image pickup module including the optical module and an image pickup device, and an endoscope including the image pickup module.

2. Description of the Related Art

An endoscope includes an image pickup module including an image pickup device such as a CCD at a distal end portion of an elongated insertion section. In recent years, use of an image pickup device including a large number of pixels in the endoscope has been examined. When the image pickup device including the large number of pixels is used, a signal amount transmitted from the image pickup device to a signal processing apparatus increases. Therefore, optical signal transmission via an optical fiber by an optical signal is desirable instead of electric signal transmission via a metal wire by an electric signal. For the optical signal transmission, an E/O optical transmission module (an electrooptic converter) that converts an electric signal into an optical signal and an O/E optical transmission module (a photoelectric converter) that converts an optical signal into an electric signal are used.

In an optical module and an image pickup module, in particular, an optical module and an image pickup module disposed at a distal end portion of an endoscope, a reduction in a diameter and a reduction in length are important problems.

For example, Japanese Patent Application Laid-Open Publication No. 2014-137584 discloses an image pickup module that converts an electric signal outputted by an image pickup device into an optical signal with a surface emitting laser (VCSEL), which is an optical element, and transmits the optical signal via an optical fiber held by a ferrule. A signal cable for transmitting an electric signal to the image pickup device and the optical element is connected to a substrate on which the image pickup device, the optical element, and the ferrule are disposed.

SUMMARY OF THE INVENTION

An optical module according to an embodiment of the present invention includes: an optical element including a light emitting section or a light receiving section; a first substrate including a first principal plane and a second principal plane facing the first principal plane, the optical element being mounted on the first principal plane; a holding member disposed on the second principal plane of the first substrate such that a center axis of a through hole coincides with an optical axis of the optical element; an optical fiber inserted into the through hole of the holding member; a holding substrate with an opening including a third principal plane and a fourth principal plane facing the third principal plane, the third principal plane being disposed in parallel to the second principal plane of the first substrate, a wall surface of the holding substrate being in contact with an outer peripheral surface of the holding member; an interconnecting substrate connecting the first substrate and the holding substrate; a side surface substrate including a fifth principal plane, which is an inner surface, and a sixth principal plane, which is an outer surface, facing the fifth principal plane, the fifth principal plane being disposed in parallel to the optical axis, an end portion of the side surface substrate being connected to the holding substrate, an electrode being disposed on at least one of the fifth principal plane and the sixth principal plane; and a signal cable, a distal end portion of which is bonded to the electrode of the side surface substrate.

An image pickup module according to another embodiment of the present invention includes: an optical module; an image pickup device including a light receiving surface and a rear surface facing the light receiving surface and configured to output an image pickup signal; a second substrate including a seventh principal plane and an eighth principal plane facing the seventh principal plane, the image pickup device being mounted on the seventh principal plane; and a second interconnecting substrate connecting the second substrate and a first substrate. The optical module includes: an optical element including a light emitting section or a light receiving section; the first substrate including a first principal plane and a second principal plane facing the first principal plane, the optical element being mounted on the first principal plane; a holding member disposed on the second principal plane of the first substrate such that a center axis of a through hole coincides with an optical axis of the optical element; an optical fiber inserted into the through hole of the holding member; a holding substrate with an opening including a third principal plane and a fourth principal plane facing the third principal plane, the third principal plane being disposed in parallel to the second principal plane of the first substrate, a wall surface of the holding substrate being in contact with an outer peripheral surface of the holding member; an interconnecting substrate connecting the first substrate and the holding substrate; a side surface substrate including a fifth principal plane, which is an inner surface, and a sixth principal plane, which is an outer surface, facing the fifth principal plane, the fifth principal plane being disposed in parallel to the optical axis, an end portion of the side surface substrate being connected to the holding substrate, an electrode being disposed on at least one of the fifth principal plane and the sixth principal plane; and a signal cable, a distal end portion of which is bonded to the electrode of the side surface substrate.

An endoscope according to still another embodiment of the present invention includes an image pickup module. The image pickup module includes: an optical module; an image pickup device including a light receiving surface and a rear surface facing the light receiving surface and configured to output an image pickup signal; a second substrate including a seventh principal plane and an eighth principal plane facing the seventh principal plane, the image pickup device being mounted on the seventh principal plane; and a second interconnecting substrate connecting the second substrate and a first substrate. The optical module includes: an optical element including a light emitting section or a light receiving section; the first substrate including a first principal plane and a second principal plane facing the first principal plane, the optical element being mounted on the first principal plane; a holding member disposed on the second principal plane of the first substrate such that a center axis of a through hole coincides with an optical axis of the optical element; an optical fiber inserted into the through hole of the holding member; a holding substrate with an opening including a third principal plane and a fourth principal plane facing the third principal plane, the third principal plane being disposed in parallel to the second principal plane of the first substrate, a wall surface of the holding substrate being in contact with an outer peripheral surface of the holding member; an interconnecting substrate connecting the first substrate and the holding substrate; a side surface substrate including a fifth principal plane, which is an inner surface, and a sixth principal plane, which is an outer surface, facing the fifth principal plane, the fifth principal plane being disposed in parallel to the optical axis, an end portion of the side surface substrate being connected to the holding substrate, an electrode being disposed on at least one of the fifth principal plane and the sixth principal plane; and a signal cable, a distal end portion of which is bonded to the electrode of the side surface substrate.

DETAILED DESCRIPTION OF THE PREFERRED EMBODIMENTS

First Embodiment

Figure 1:
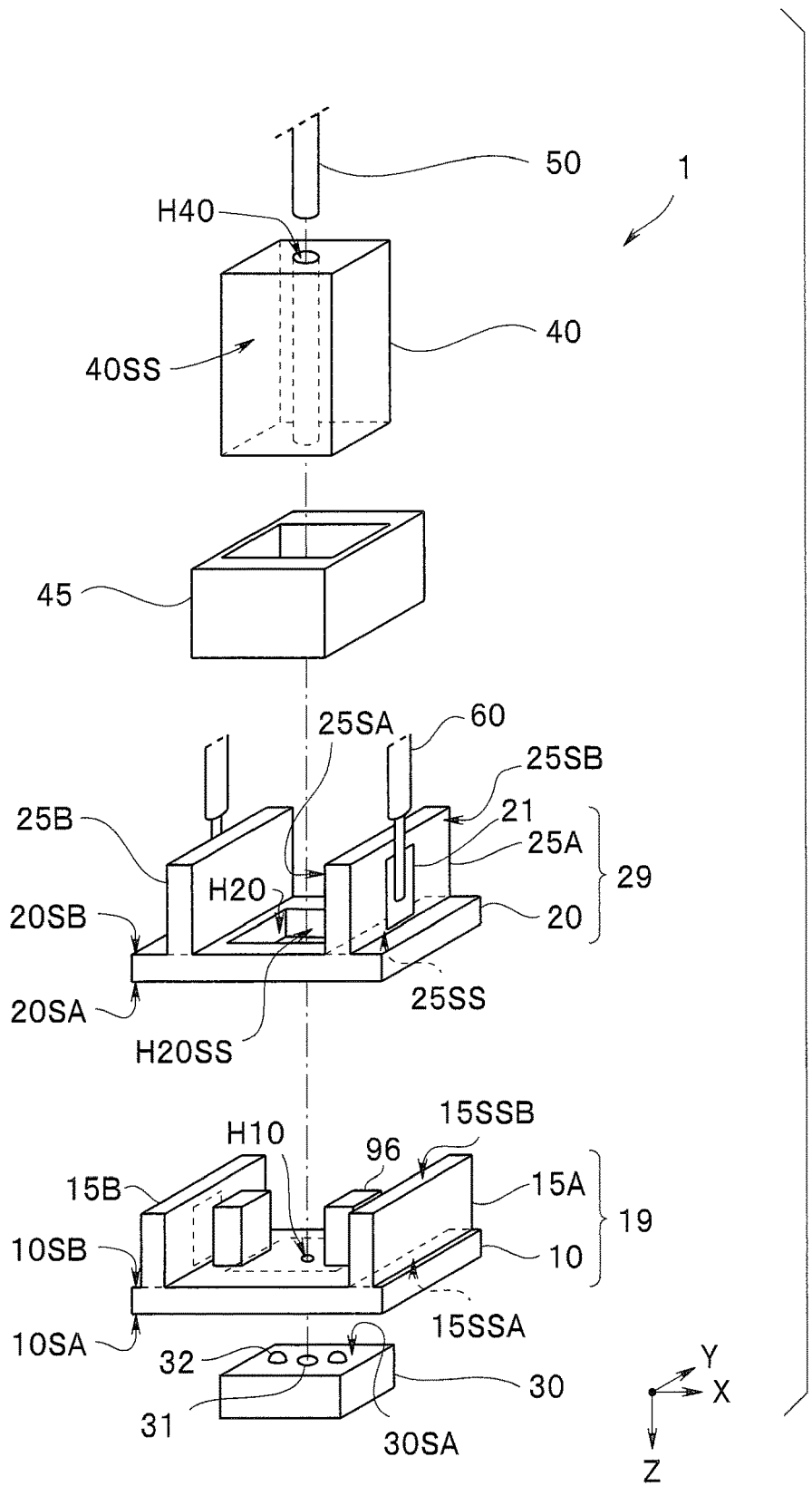
FIG. 1 is an exploded view of an optical module in a first embodiment.
Figure 2:
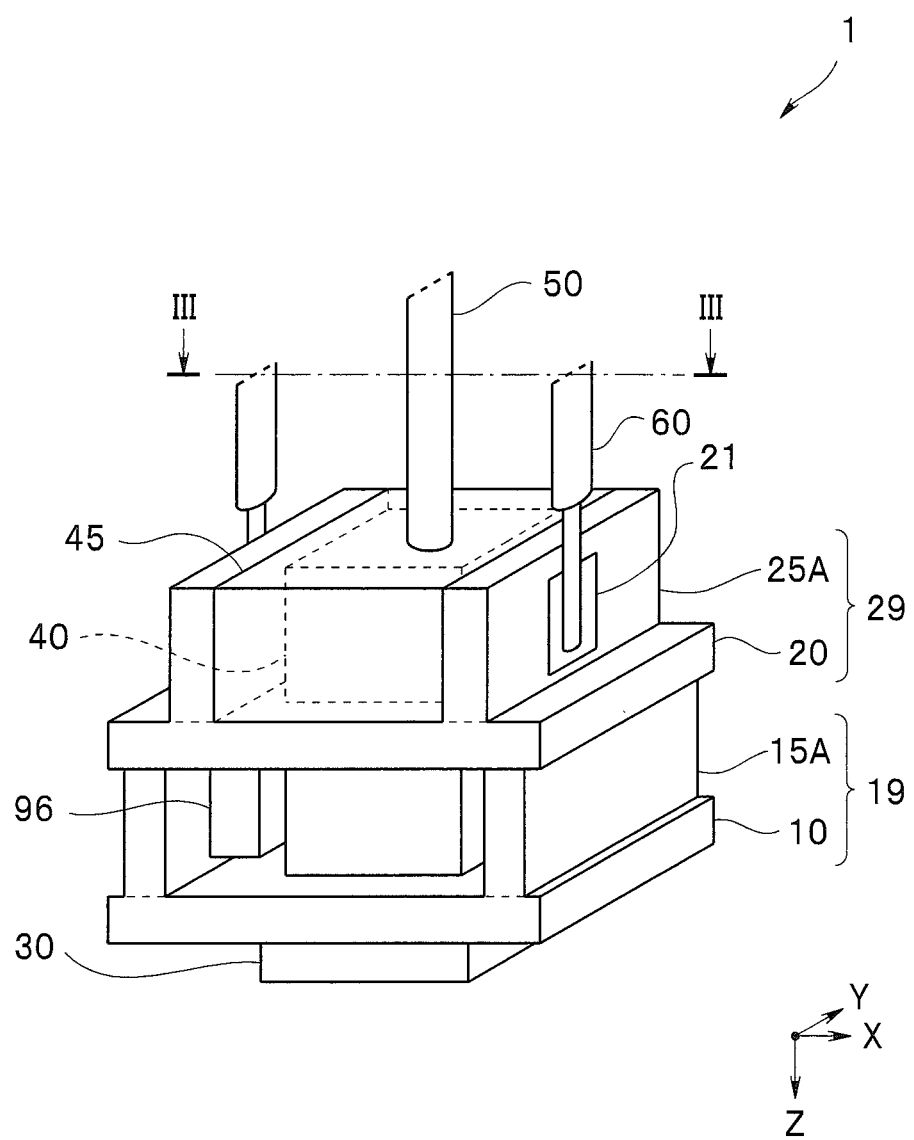
FIG. 2 is a perspective view of the optical module in the first embodiment.

An optical module 1 in this embodiment is explained with reference to FIG. 1 to FIG. 3. The optical module 1 is an E/O module that converts an electric signal into an optical signal and transmits the optical signal.

Note that all the drawings are schematic and relations between thicknesses and widths of respective portions, ratios of thicknesses of the respective portions, and the like are different from real ones. Portions, relations and ratios of dimensions of which are different from one another, are sometimes included among the drawings. Illustration of a part of components, for example, a wire and a resin member (45) of a substrate is sometimes omitted.

The optical module 1 includes an optical element 30, a first substrate 10, interconnecting substrates 15A and 15B, a holding substrate 20, side surface substrates 25A and 25B, a ferrule 40, which is a holding member, an optical fiber 50, and signal cables 60. As explained below, the first substrate 10 and the interconnecting substrates 15A and 15B are an integral three-dimensional substrate 19. The holding substrate 20 and the side surface substrates 25A and 25B are an integral three-dimensional substrate 29.

Note that when each of a plurality of components having the same configuration is referred to, one character at the end of a sign is sometimes omitted. For example, each of the side surface substrates 25A and 25B is referred to as side surface substrate 25.

The optical element 30 is a VCSEL (vertical cavity surface emitting laser) including a light emitting section 31 that outputs an optical signal along an optical axis O perpendicular to a front surface 30SA. The optical element 30 is an ultra-small type, a size of a cross section in an optical axis orthogonal direction, that is, a plan view dimension of which is 250 μm×250 μm. The optical element 30 includes, on the front surface 30SA, a light emitting section 31 having a diameter of 10 μm and two external terminals 32 having a diameter of 70 μm connected to the light emitting section 31.

For example, the signal cables 60 transmit electric signals to the optical element 30. Lead wires at distal end portions of the signal cables 60 are bonded to electrodes 21 of the side surface substrates 25A and 25B via not-shown solder. In other words, the electrodes 21 and the distal end portions of the signal cables 60 are disposed in parallel to the optical axis O (a Z axis).

For example, the optical fiber 50 includes a core having a diameter of 50 μm that transmits an optical signal and a clad having a diameter of 125 μm that covers the outer circumference of the core.

The ferrule 40 is a rectangular parallelepiped, a sectional shape of which in the optical axis orthogonal direction is a rectangle. The ferrule 40 includes four side surfaces 40SS. A through hole H40 piercing through an upper surface and a lower surface is present in the ferrule 40. A distal end portion of the optical fiber 50 is inserted into the through hole H40 and fixed by an adhesive.

The first substrate 10 includes a first principal plane 10SA and a second principal plane 10SB facing the first principal plane 10SA. The optical element 30 is mounted on the first principal plane 10SA. In other words, although not shown in the figures, the external terminal 32 of the optical element 30 is bonded to a bonding electrode on the first principal plane 10SA. The ferrule 40 is bonded to the second principal plane 10SB.

The front surface 30SA of the optical element 30 is parallel to the first principal plane 10SA (an XY plane) of the first substrate 10. In other words, the optical axis O is parallel to a Z axis perpendicular to the first principal plane 10SA. Note that the first substrate 10 does not have high light transmittance. Therefore, a through hole H10 functioning as an optical path is formed in the first substrate 10.

The holding substrate 20 includes a third principal plane 20SA and a fourth principal plane 20SB facing the third principal plane 20SA. The third principal plane 20SA and the fourth principal plane 20SB are disposed in parallel to the second principal plane 10SB and the first principal plane 10SA of the first substrate 10.

In the holding substrate 20, an opening (a second through hole) H20 having a rectangular shape in plan view is present. A dimension in the optical axis orthogonal direction, that is, a plan view size of the opening H20 is the same as or slightly larger than a plan view size of the ferrule 40. Therefore, four outer peripheral surfaces (side surfaces) 40SS of the ferrule 40 having a quadrangular prism shape inserted into the opening H20 are in contact with four wall surfaces H20SS of the opening H20 having the rectangular shape in plan view.

The interconnecting substrates 15A and 15B disposed to be facing each other have substantially the same configuration. The interconnecting substrate 15 connects the first substrate 10 and the holding substrate 20. In other words, a principal plane of the interconnecting substrate 15 is disposed in parallel to the optical axis O (the Z axis). A lower end face 15SSA of the interconnecting substrate 15 is disposed in an outer peripheral portion of the second principal plane 10SB of the first substrate 10. An upper end face 15SSB of the interconnecting substrate 15 is connected to an outer peripheral portion of the third principal plane 20SA of the holding substrate 20.

The side surface substrates 25A and 25B disposed to be facing each other have substantially the same configuration. An end face of the side surface substrate 25 is disposed in an outer peripheral portion of the fourth principal plane 20SB of the holding substrate 20. In other words, a fifth principal plane (an inner surface) 25SA and a sixth principal plane (an outer surface) 25SB of the side surface substrate 25 are disposed in parallel to the optical axis O (the Z axis).

The electrodes 21 are respectively disposed on the sixth principal planes 25SB of the side surface substrates 25A and 25B. The electrodes 21 are electrically connected to the optical element 30 and the like via wires (not shown in the figures). The number of electrodes 21 is the same as the number of signal cables 60.

Positioning of the light emitting section 31 of the optical element 30 and the optical fiber 50 is performed by inserting and fitting the optical fiber 50 into the through hole H40. In other words, the ferrule 40 is disposed on the second principal plane 10SB of the first substrate 10 in a state in which the center axis of the through hole H40 is disposed to coincide with an optical axis of the optical element 30. An inner shape of the through hole H40 may be, besides a columnar shape, a prism shape such as a quadrangular prism shape or a hexagonal prism shape as long as the optical fiber 50 can be held by the wall surface of the through hole H40.

A resin member 45 is filled in a space that is surrounded by the side surface substrates 25A and 25B and in which the ferrule 40 is disposed. The resin member 45 is made of, for example, epoxy resin. Note that the resin member 45 is not an essential component of the optical module. However, the optical module 1 in which the ferrule 40 is firmly fixed by the resin member 45 has higher reliability.

In the optical module 1, the four outer peripheral surfaces (the side surfaces) 40SS of the ferrule 40 are in contact with the four wall surfaces H20SS of the opening H20 of the holding substrate 20. Consequently, positioning in an in-plane direction (an XY direction) of the ferrule 40 is performed. At the same time, the ferrule 40 is stably held.

Therefore, the optical module 1 has high transmission efficiency and reliability.

As explained above, the first substrate 10 and the interconnecting substrates 15A and 15B are the integral three-dimensional substrate 19 made of ceramic and have not-shown wires. The holding substrate 20 and the side surface substrates 25A and 25B are the integral three-dimensional substrate 29 made of ceramic.

The three-dimensional substrates 19 and 29 may be configured by a molded circuit component (MID: molded interconnect device) having nonconductive resin as a base material and including wires (not shown in the figures) and electrodes.

The first substrate 10 and the interconnecting substrate 15 are accurately and firmly connected to the three-dimensional substrates 19 and 29. Therefore, the optical module 1 is easily manufactured.

Figure 3:
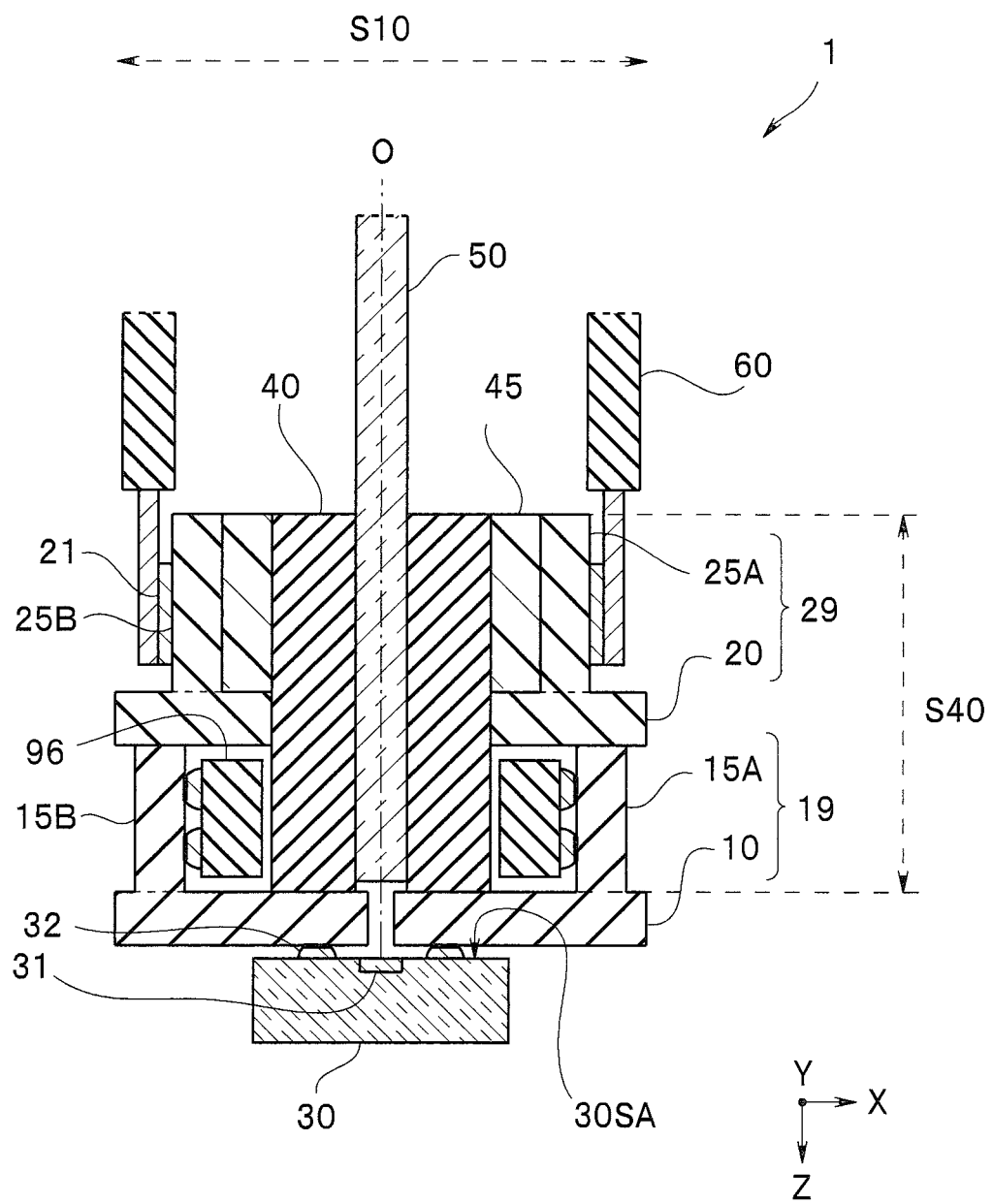
FIG. 3 is a sectional view taken along a III-III line of FIG. 2 of the optical module in the first embodiment.

As shown in FIG. 3, the optical element 30, the ferrule 40, the holding substrate 20, the interconnecting substrates 15A and 15B, the side surface substrates 25A and 25B, and the distal end portions of the signal cables 60 are included in a first space S10 formed by extending the first substrate 10 in the direction of the optical axis O. Therefore, the optical module 1 is small in the optical axis orthogonal direction and has a small diameter.

Further, the electrodes 21 of the side surface substrates 25A and 25B, that is, bonded sections of the signal cables 60 are included in a second space S40 formed by extending the ferrule 40 in the direction orthogonal to the optical axis O. Therefore, the optical module 1 is short and small.

Further, in the optical module 1, an electronic component 96, which is a chip-shaped surface mounted device (SMD) such as a capacitor, an inductor, or a signal processing IC is mounted on the inner side surface of the interconnecting substrate 15. In other words, there is a gap between the interconnecting substrate 15 and the ferrule 40 since the first substrate 10 of the optical module 1 is large. The electronic component 96 is disposed in the gap.

In the optical module 1, since the electronic component 96 is mounted in a place near the optical element 30, a wire between the optical element 30 and the electronic component 96 is short. Therefore, for example, the optical module 1 is less easily affected by noise.

The material of the ferrule 40 is a metal member such as SUS, ceramic, silicon, or glass. As explained below, the ferrule 40 may be a substantial column, cone, or prism. The plan view shape of the opening of the holding substrate is designed according to a shape of the ferrule. For example, when the ferrule is a regular hexagonal prism, the opening of the holding substrate is a regular hexagonal in plan view.

As explained above, the side surface substrates 25A and 25B are disposed to be facing each other to surround the ferrule 40, which is the holding member. Note that the distances from the optical axis O to the side surface substrates 25A and 25B do not have to be the same. The shapes (widths/thicknesses) of the side surface substrate 25A and the side surface substrate 25B may be different.

The number of side surface substrates 25 only has to be one or more and four or less but, in particular, is desirably two or more. A plurality of side surface substrates 25 may be disposed in orthogonal positions or facing positions as long as the plurality of side surface substrates 25 are disposed to surround the ferrule 40. For example, when the optical module 1 includes three side surface substrates 25, two side surface substrates are disposed in facing positions and one side surface substrate is disposed in a position orthogonal to the two side surface substrates.

In the side surface substrate 25, the electrode 21 is disposed on at least one of the fifth principal plane 25SA and the sixth principal plane 25SB. When the optical module 1 includes a plurality of side surface substrates, the electrode 21 only has to be disposed on at least any one side surface substrate 25.

The number of interconnecting substrates 15 only has to be one or more and four or less but, in particular, is desirably two or more in order to stably hold the first substrate 10 and the holding substrate 20. Respective principal planes of a plurality of interconnecting substrates 15 are desirably disposed in orthogonal positions or facing positions.

Note that, in the optical module 1, the optical element is a light emitting element including a light emitting section. However, it goes without saying that an optical module in which an optical element is a light receiving element including a light receiving section such as a photodiode has the same effects as the effects of the optical module 1.

Modifications of the First Embodiment

Optical modules in modifications of the first embodiment are similar to the optical module 1 and have the same effects as the effects of the optical module 1. Therefore, components having the same functions are denoted by the same reference numerals and signs and explanation of the components is omitted.

Modification 1 of the First Embodiment

Figure 4:
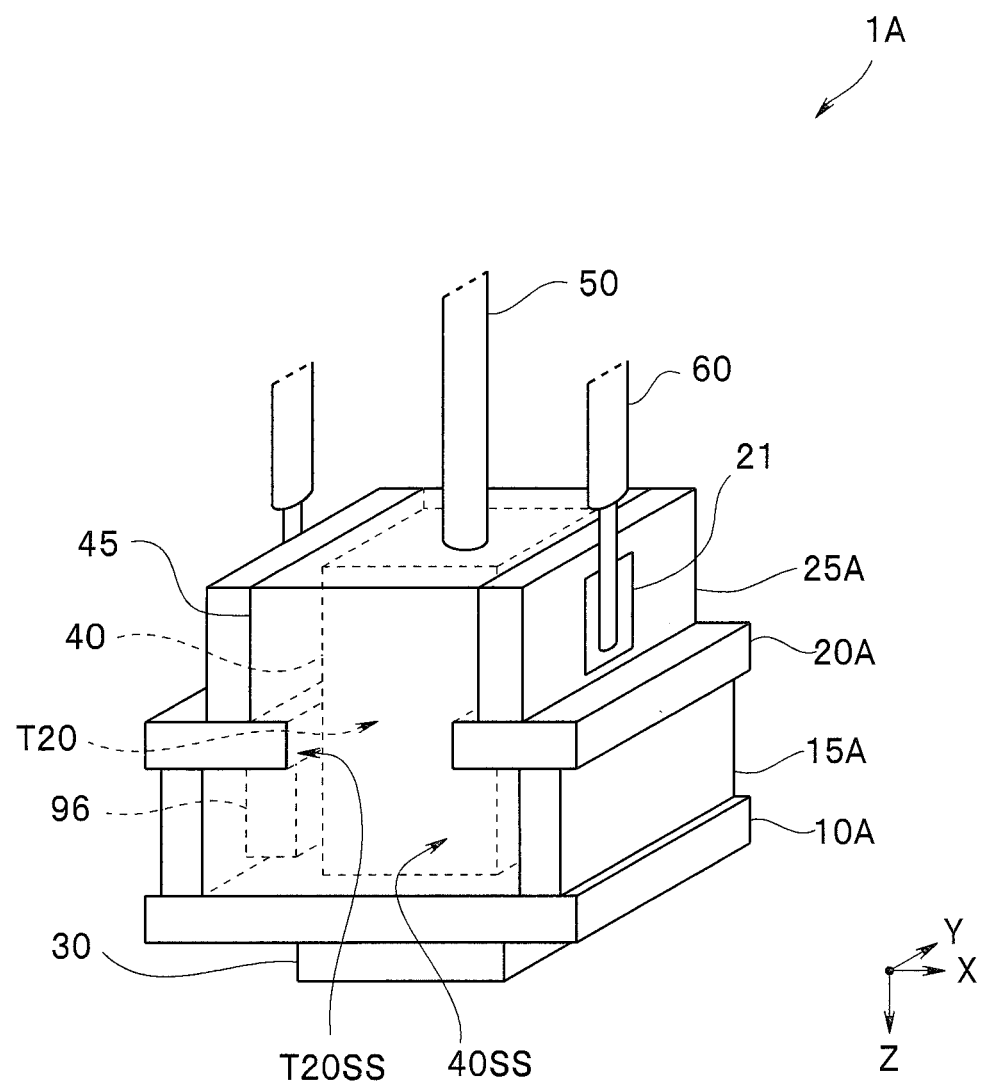
FIG. 4 is a perspective view of an optical module in a modification 1 of the first embodiment.
Figure 5:
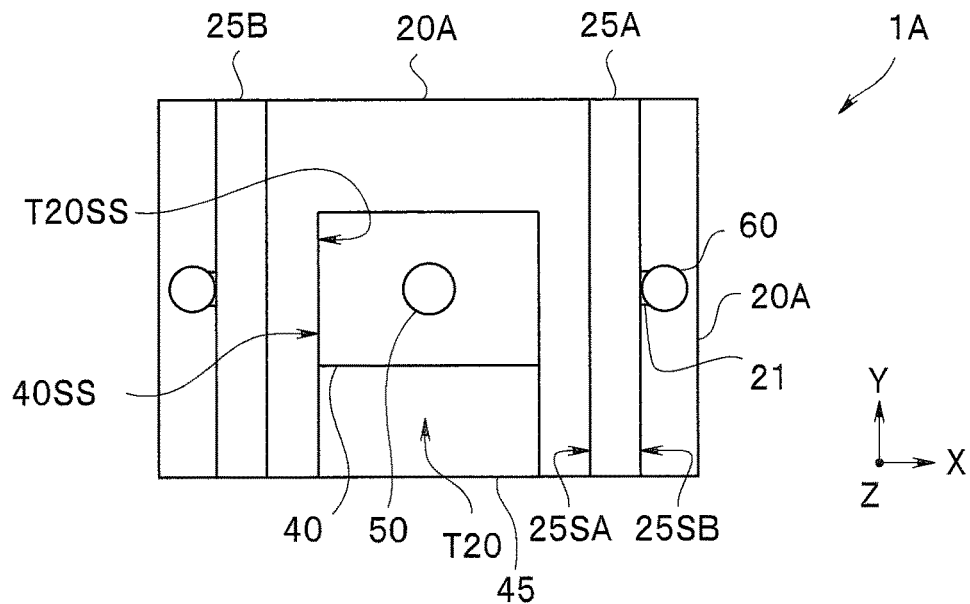
FIG. 5 is a transparent top view of the optical module in the modification 1 of the first embodiment.

As shown in FIG. 4 and FIG. 5, in an optical module 1A in this modification, an opening of a holding substrate 20A is a cutout T20 having a rectangular shape in plan view. In other words, three inner peripheral surfaces of the opening with which three outer peripheral surfaces (side surfaces) 40SS of the ferrule 40 are in contact are three wall surfaces T20SS of the cutout T20 of the holding substrate 20A.

In other words, the opening of the holding substrate 20A may be either the second through hole H20 or the cutout T20 as long as the opening has a positioning function and a holding function for the ferrule 40.

A first substrate 10A, the interconnecting substrate 15, the holding substrate 20A, and the side surface substrates 25A and 25B are FPC substrates, ceramic substrates, glass epoxy substrates, glass substrates, silicon substrates, or the like. For example, an end face of the interconnecting substrate 15A is fixed to the second principal plane 10SB of the first substrate 10A by an adhesive. A wire of the first substrate 10A and a wire of the interconnecting substrate 15A conduct via, for example, conductive paste.

Modification 2 of the First Embodiment

Figure 6:
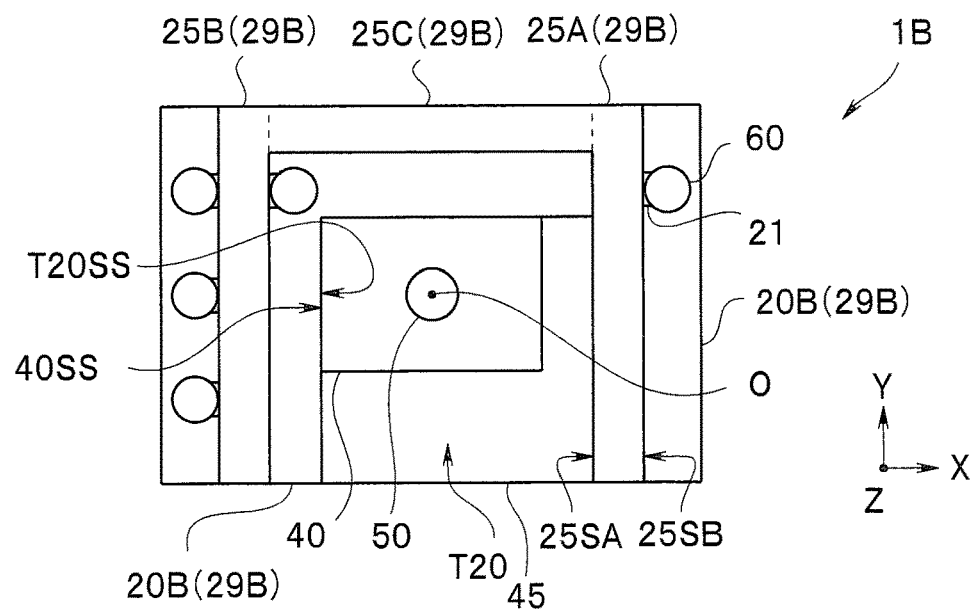
FIG. 6 is a transparent top view of an optical module in a modification 2 of the first embodiment.

As shown in FIG. 6, an optical module 1B in this modification includes three side surface substrates 25A, 25B, and 25C. Principal planes of the side surface substrates 25A and 25B are disposed in facing positions, that is, rotational symmetrical positions. A principal plane of the side surface substrate 25C is disposed in a position orthogonal to the principal planes of the side surface substrates 25A and 25B.

Note that the side surface substrates 25A, 25B, and 25C and a holding substrate 20B are configured by an integral three-dimensional substrate 29B made of ceramic. Therefore, the side surface substrates 25A, 25B, and 25C are a U-shaped integral structure. Boundaries of the side surface substrates 25A, 25B, and 25C are unclear.

Two side surfaces 40SS of the ferrule 40 are in contact with two wall surfaces T20SS of the cutout T20. Positioning in an in-plane direction of the ferrule 40 is easy if at least two side surfaces 40SS of the ferrule 40 are in contact with the two wall surfaces T20SS of the cutout T20.

The electrode 21 to which the signal cable 60 is bonded is present on the fifth principal plane (the inner surface) 25SA of the side surface substrate 25B as well. Note that the electrode 21 may be disposed on only the fifth principal plane (the inner surface) 25SA of the side surface substrate 25B. In other words, the electrode 21 only has to be disposed on at least one of the fifth principal plane (the inner surface) 25SA and the sixth principal plane (the outer surface) 25SB of the side surface substrate 25B.

Modification 3 of the First Embodiment

Figure 7:
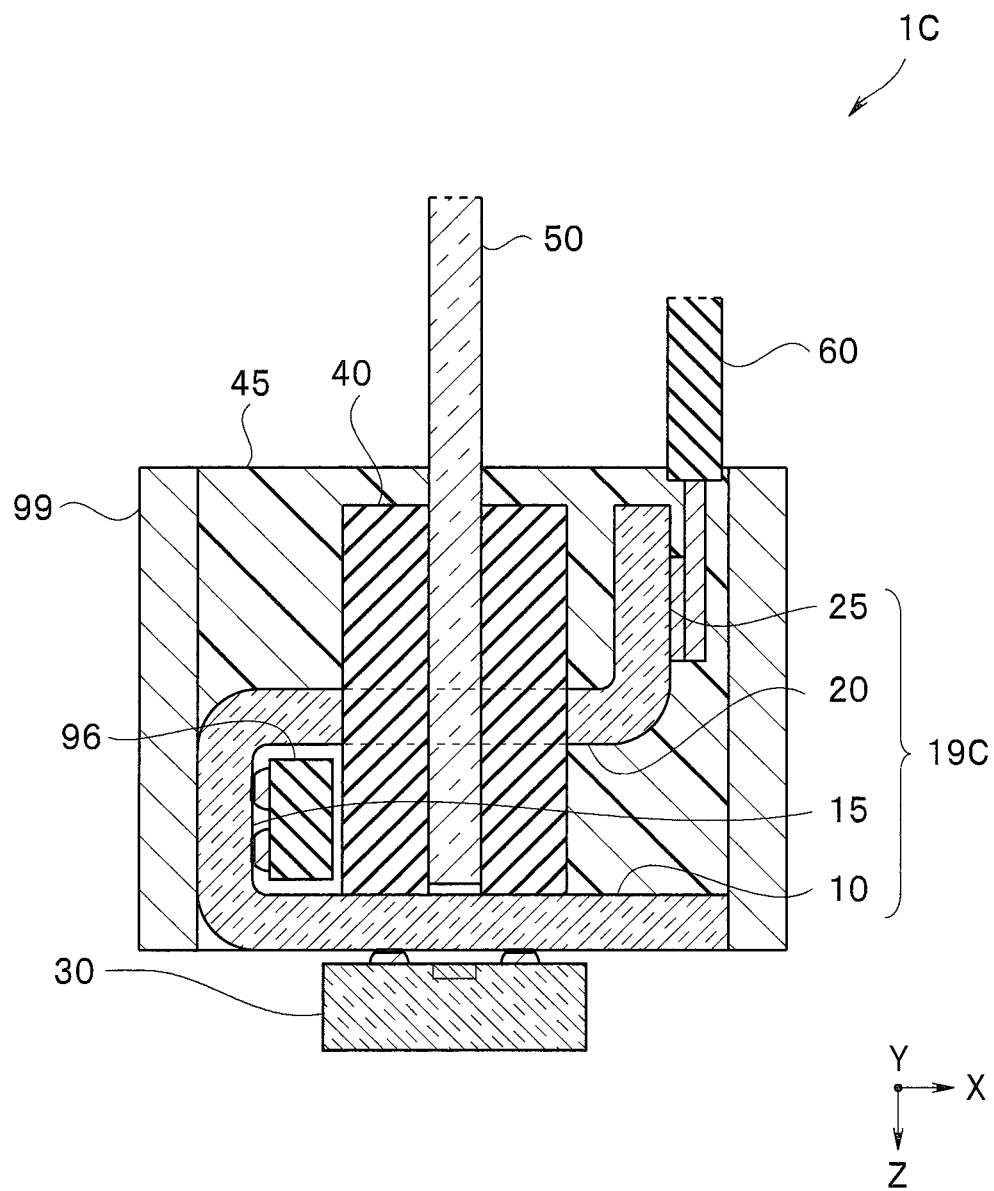
FIG. 7 is a sectional view of an optical module in a modification 3 of the first embodiment.

As shown in FIG. 7, in an optical module 1C in this modification, the first substrate 10, the interconnecting substrate 15, the holding substrate 20, and the side surface substrate 25 are a flexible integral three-dimensional substrate 19C. The three-dimensional substrate 19C may be a multilayer substrate, on not only both surfaces but also on an inside of which wires are present. Note that a through hole functioning as an optical path of an optical signal is not formed in the three-dimensional substrate 19C since a base body is made of a light transmissive material such as polyimide. In other words, the through hole of the first substrate is not an essential component.

In the optical module 1C, the three-dimensional substrate 19C and the like are disposed on an inside of a housing 99, which is a tubular member. The resin 45 is filled in an internal space of the housing 99.

In the optical module 1C, the optical element 30, the signal cables 60, and the ferrule 40 can be disposed on the flat substrate 19C. The substrate 19C is formed three-dimensionally by disposing a constituent member and thereafter bending connecting sections. The substrate 19C is disposed on the inside of the housing 99. Therefore, the optical module 1C is easily manufactured.

Note that the housing 99 may be a member common to other members rather than a member exclusive for the optical module 1C. For example, the substrate 19C and the like may be inserted into a through hole formed at a distal end hard portion of an endoscope and may be fixed by the resin 45.

Second Embodiment

Figure 8:
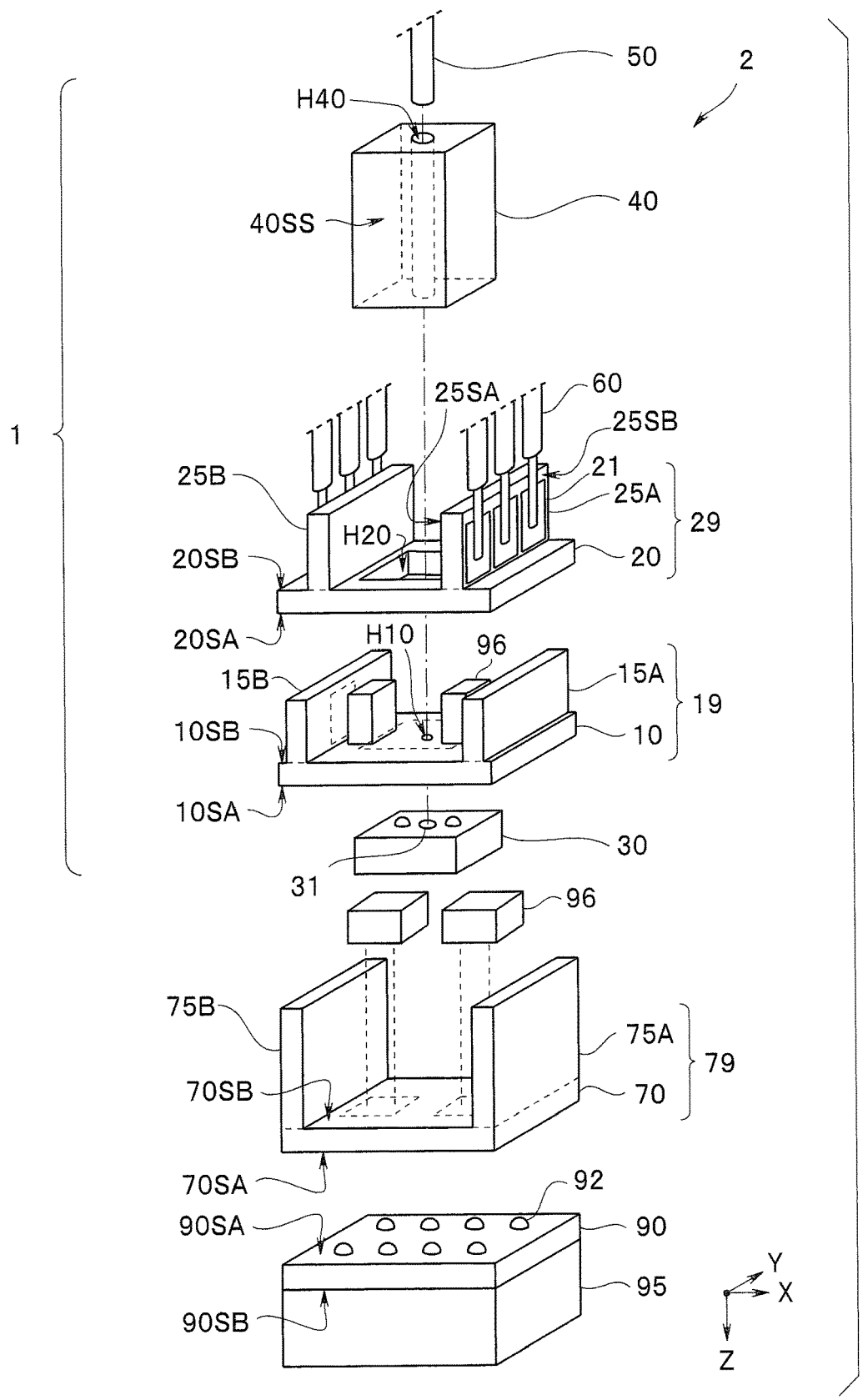
FIG. 8 is an exploded view of an image pickup module in a second embodiment.
Figure 9:
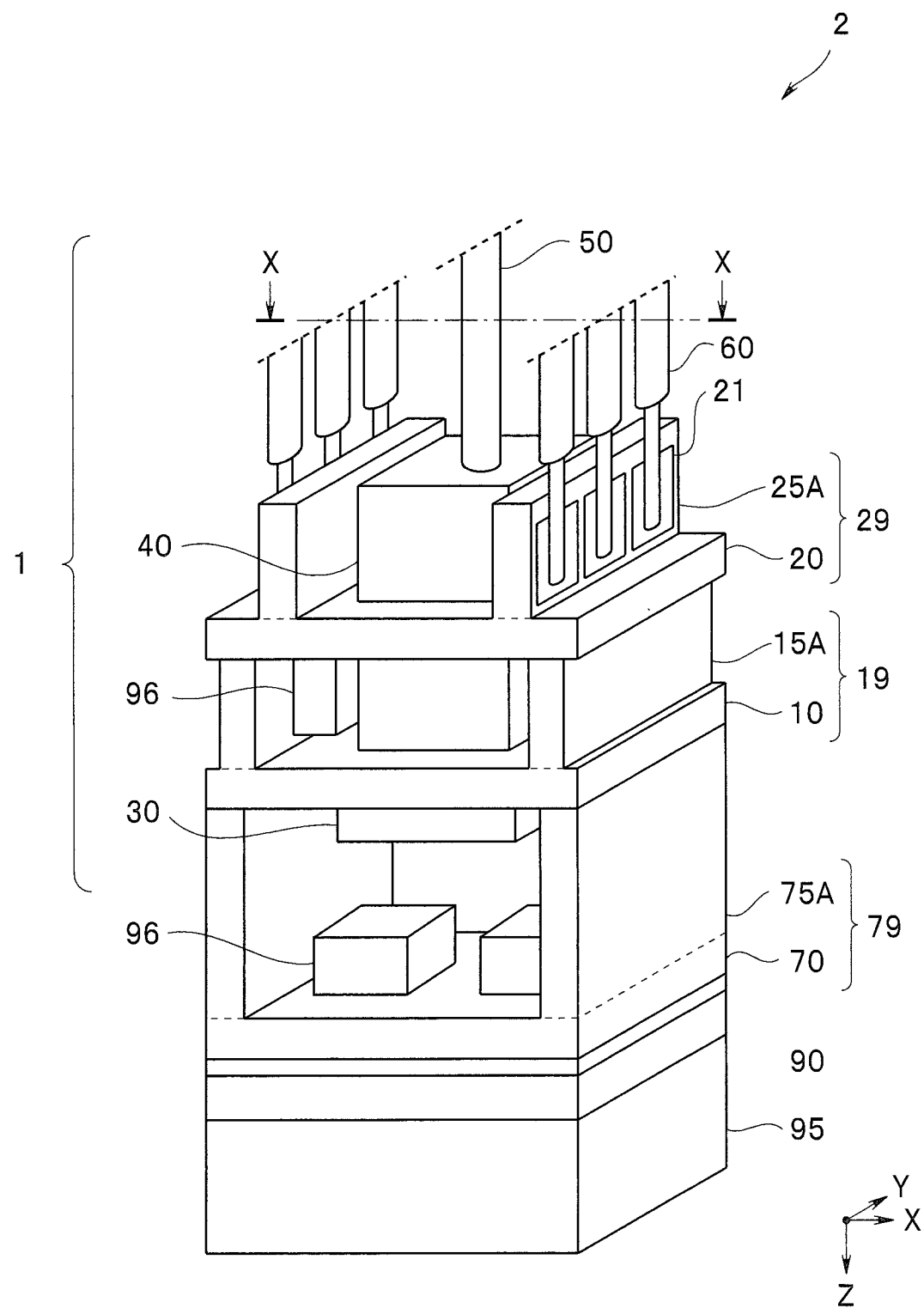
FIG. 9 is a perspective view of the image pickup module in the second embodiment.
Figure 10:
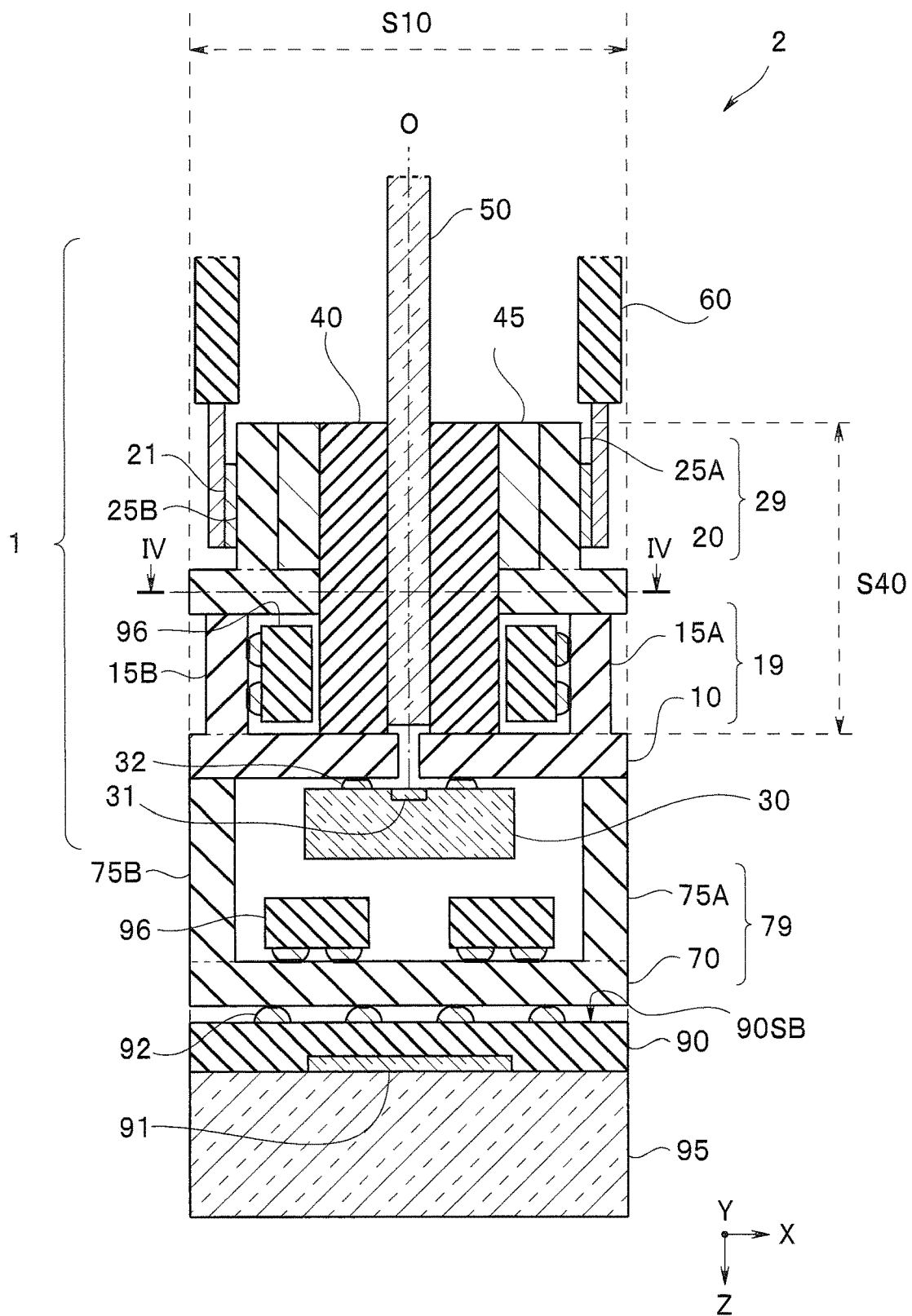
FIG. 10 is a sectional view taken along a X-X line of FIG. 9 of the image pickup module in the second embodiment.

As shown in FIG. 8 to FIG. 10, an image pickup module 2 in this embodiment includes the optical module 1 in the first embodiment, an image pickup device 90, a second substrate 70, and second interconnecting substrates 75A and 75B.

The signal cables 60 transmit electric signals to the image pickup device 90 and the like. An image pickup signal output by the image pickup device 90 is converted into an optical signal by the optical element 30 and transmitted via the optical fiber 50.

The image pickup device 90 includes a light receiving surface 90SA and a rear surface 90SB facing the light receiving surface 90SA and outputs an image pickup signal. A light receiving section 91 such as a CCD or CMOS light reception circuit is formed on the light receiving surface 90SA of the image pickup device 90. The light receiving section 91 is connected to a bonding terminal 92 of the rear surface 90SB via a through wire (not shown in the figures) by TSV (through-silicon via) or the like. A cover glass 95 for protecting the light receiving section 91 is bonded to the light receiving surface 90SA. Note that the cover glass 95 is not an essential component of the image pickup module 2.

The second substrate 70 includes a seventh principal plane 70SA and an eighth principal plane 70SB facing the seventh principal plane 70SA. The image pickup device 90 is bonded to the seventh principal plane 70SA.

The second interconnecting substrates 75A and 75B connect the first substrate 10 and the second substrate 70. In other words, in this embodiment, the image pickup module 2 includes two second interconnecting substrates 75A and 75B having the same configuration. One end face of the second interconnecting substrate 75 is disposed perpendicularly to the first principal plane 10SA of the first substrate 10. The other end face of the second interconnecting substrate 75 is disposed perpendicularly to the eighth principal plane 70SB of the second substrate 70.

Note that, in this embodiment, the second substrate 70 and the second interconnecting substrates 75A and 75B are an integral three-dimensional substrate 79 made of ceramic. The three-dimensional substrate 79 may be a molded circuit component.

As shown in FIG. 10, the second substrate 70, the second interconnecting substrate 75, the first substrate 10, the interconnecting substrate 15, the holding substrate 20, the side surface substrates 25A and 25B, the optical element 30, the ferrule 40, and the distal end portions of the signal cables 60 are included in the space S10 formed by extending the image pickup device 90 in the optical axis O direction. Therefore, the image pickup module 2 has a small diameter.

In particular, the image pickup device 90 including a large number of pixels has a large plan view size. Therefore, it is possible to easily dispose the side surface substrates 25A and 25B and the signal cables 60 around the ferrule 40.

Further, the electrodes 21 of the side surface substrates 25A and 25B, that is, the bonded sections of the signal cables 60 are included in a second space S40 formed by extending the ferrule 40 in a direction orthogonal to the optical axis O. Therefore, the image pickup module 2 is short and small.

As explained above, the image pickup module 2 is small in diameter and short and small and has high transmission efficiency and high reliability.

Note that the optical element 30 is housed in a space formed by the second interconnecting substrates 75A and 75B. In this embodiment, the chip-shaped electronic component 96 such as a capacitor, an inductor, or a signal processing IC is mounted on the eighth principal plane 70SB of the second substrate 70 facing the rear surface 90SB of the image pickup device 90. The electronic component 96 is housed in the same space as the optical element 30.

The distance between the image pickup device 90 and the electronic component 96 is slightly larger than the thickness of the second substrate 70. The image pickup device 90 and the electronic component 96 are close to each other. If, for example, a decoupling capacitor is disposed in a position close to the image pickup device 90, it is possible to efficiently reduce the influence of noise.

Note that the electronic component 96 may be mounted on the principal plane of any of the first substrate 10, the second substrate 70, the side surface substrates 25A and 25B, and the second interconnecting substrates 75A and 75B as long as the electronic component 96 is present in the space S10 formed by extending the image pickup device 90 in the optical axis O direction.

Modifications of the Second Embodiment

Image pickup modules 2A to 2D in modifications of the second embodiment are similar to the image pickup module 2 and have the same effects as the effects of the image pickup module 2. Therefore, components having the same functions are denoted by the same reference numerals and signs and explanation of the components is omitted.

Modification 1 of the Second Embodiment

Figure 11:
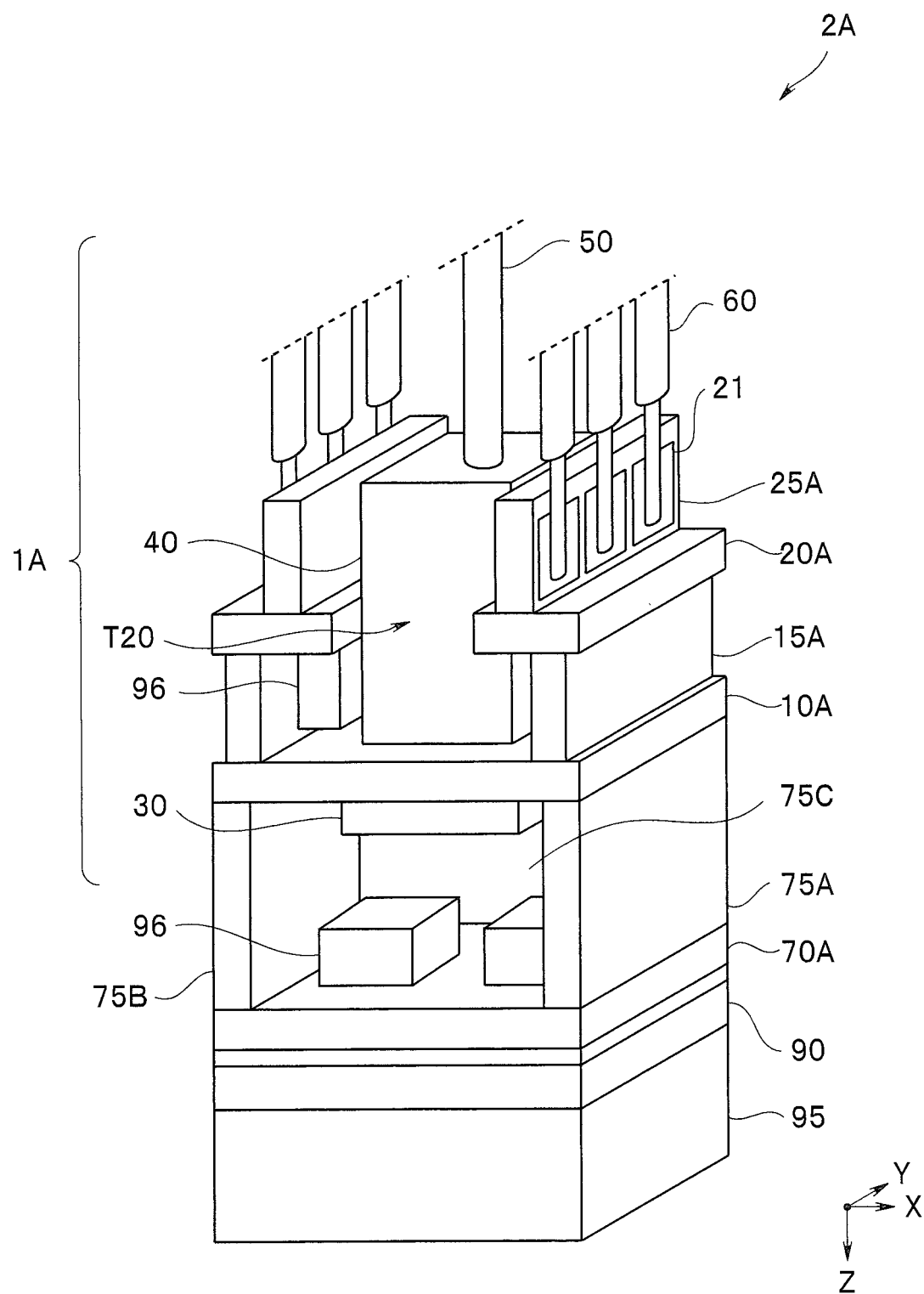
FIG. 11 is a perspective view of an image pickup module in a modification 1 of the second embodiment.

As shown in FIG. 11, the image pickup module 2A in a modification 1 of the second embodiment includes the optical module 1A, the image pickup device 90, a second substrate 70A, and three second interconnecting substrates 75A to 75C. The second interconnecting substrates 75A and 75B are disposed in facing positions. The second interconnecting substrates 75A and 75C are disposed in orthogonal positions.

A principal plane of the second interconnecting substrate 75 that connects the first substrate 10A and the second substrate 70A is disposed in parallel to the optical axis O. The principal plane is disposed perpendicularly to the first principal plane 10SA and the eighth principal plane 70SB.

Note that the number of second interconnecting substrates 75 only has to be one to four like the side surface boards and the like of the optical module 1 explained above.

Modification 2 of the Second Embodiment

Figure 12:
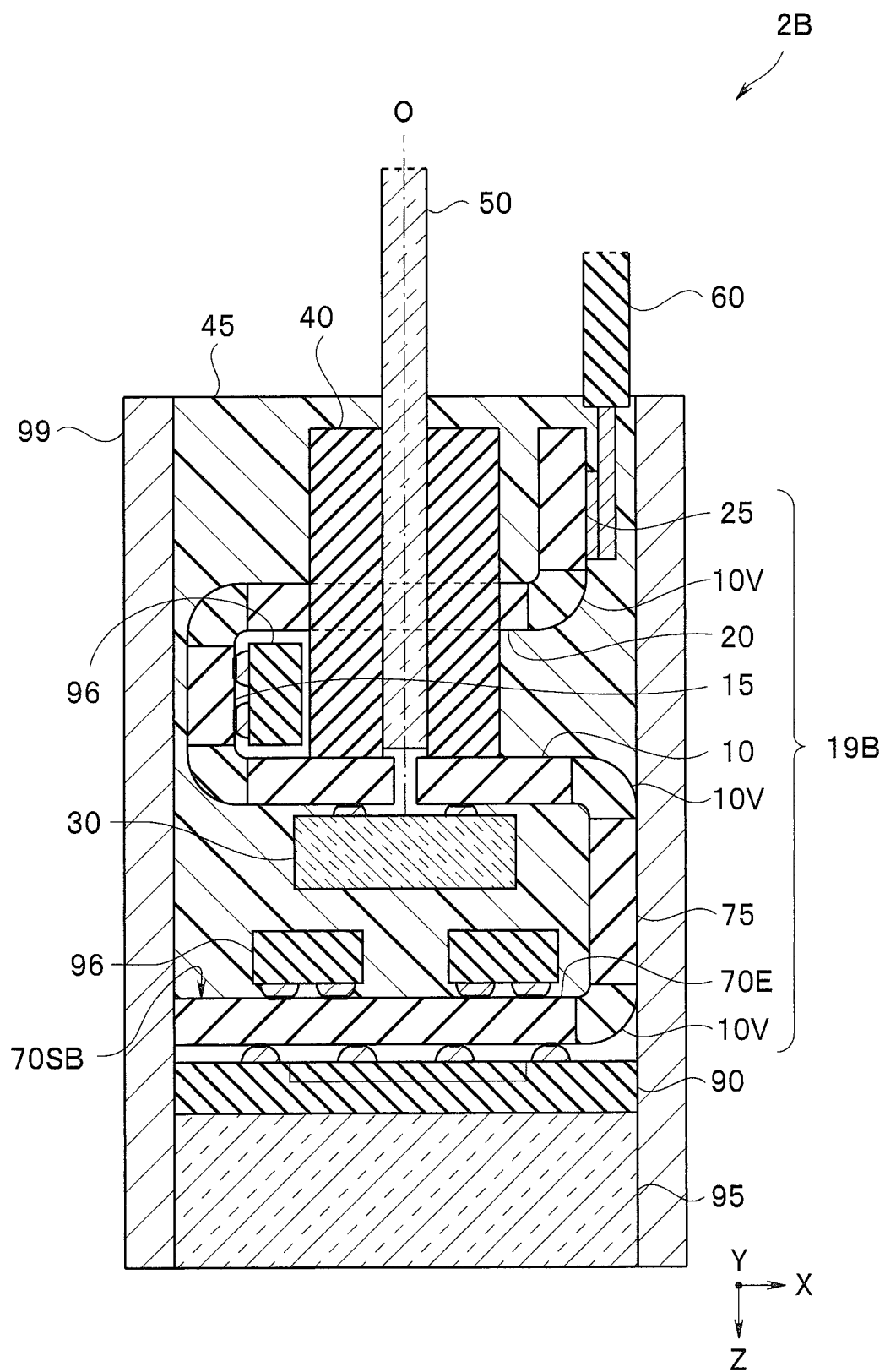
FIG. 12 is a sectional view of an image pickup module in a modification 2 of the second embodiment.
Figure 13:
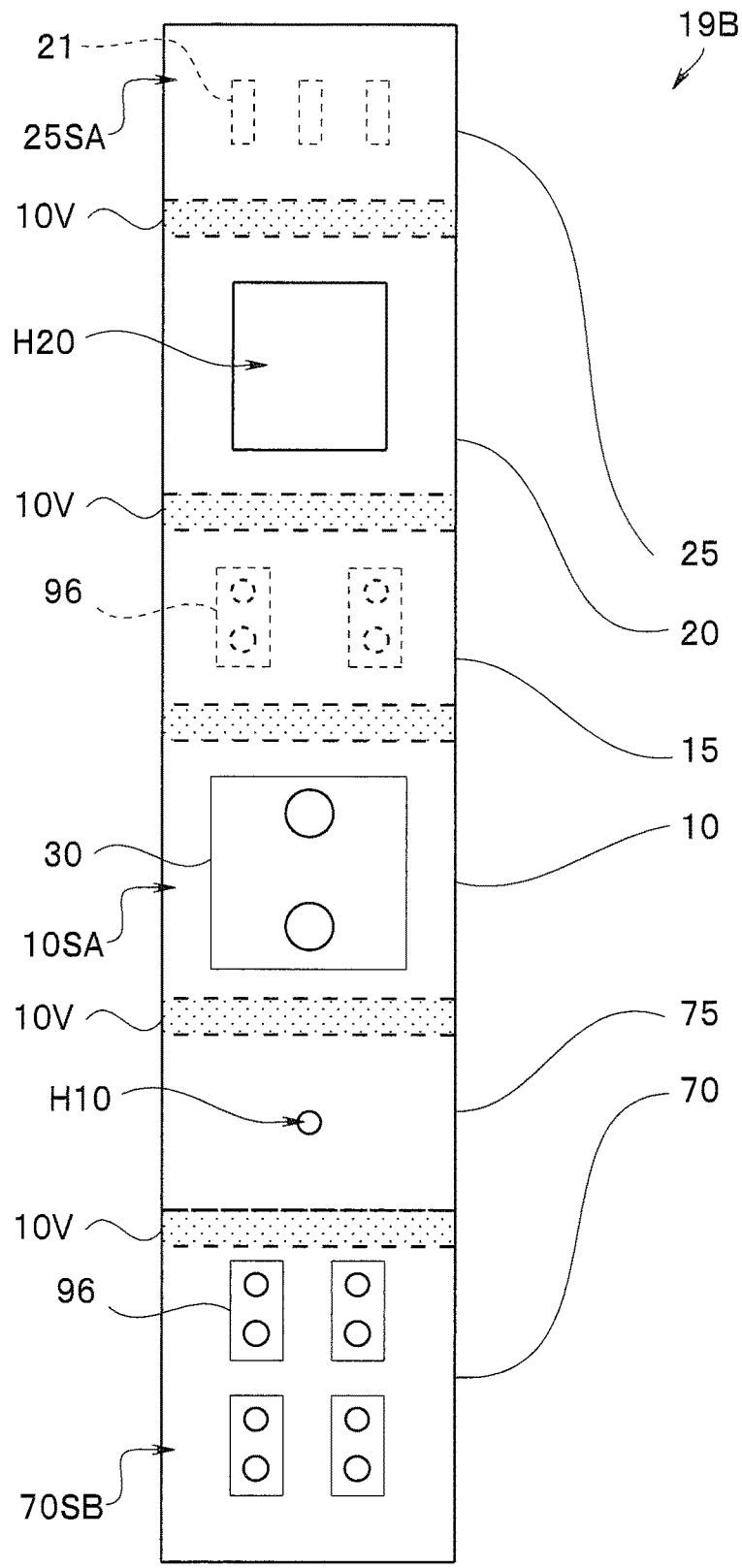
FIG. 13 is a development diagram of a substrate of the image pickup module in the modification 2 of the second embodiment.

As shown in FIG. 12 and FIG. 13, the image pickup module 2B in a modification 2 of the second embodiment is similar to the optical module 1C. In the image pickup module 2B, the second substrate 70, the second interconnecting substrate 75, the first substrate 10, the interconnecting substrate 15, the holding substrate 20, and the side surface substrate 25 are respectively concatenated via flexible connecting sections 10V and are an integrated substrate 19B, a so-called rigid flexible substrate having advantages of both of a rigid substrate and a flexible substrate.

In the image pickup module 2B, the image pickup device 90 and the like are housed in a hollow section of the housing 99 and sealed by the resin 45. The electronic component 96 is mounted on the eighth principal plane 70SB of a second substrate 70E.

The connecting sections 10V of the substrate 19B are flexible substrates having, for example, polyimide as a base body. On the other hand, the second substrate 70, the second interconnecting substrate 75, the first substrate 10, the interconnecting substrate 15, the holding substrate 20, and the side surface substrate 25 are rigid substrates. The through hole H10 functioning as an optical path is present in the first substrate 10.

The flat substrate 19B shown in FIG. 13 is formed as a three-dimensional substrate by bending connecting sections. Before the bending, an image pickup device, an optical element, a signal cable, a ferrule, and the like can be disposed on the flat substrate 19B. Therefore, the image pickup module 2B is easily manufactured.

Note that the entire three-dimensional substrate 19B may be flexible or the three-dimensional substrate 19B may be a multilayer substrate. The three-dimensional substrate 19B may include one to four side surface substrates, one to four interconnecting substrates, and one to four second interconnecting substrates.

Modification 3 of the Second Embodiment

Figure 14:
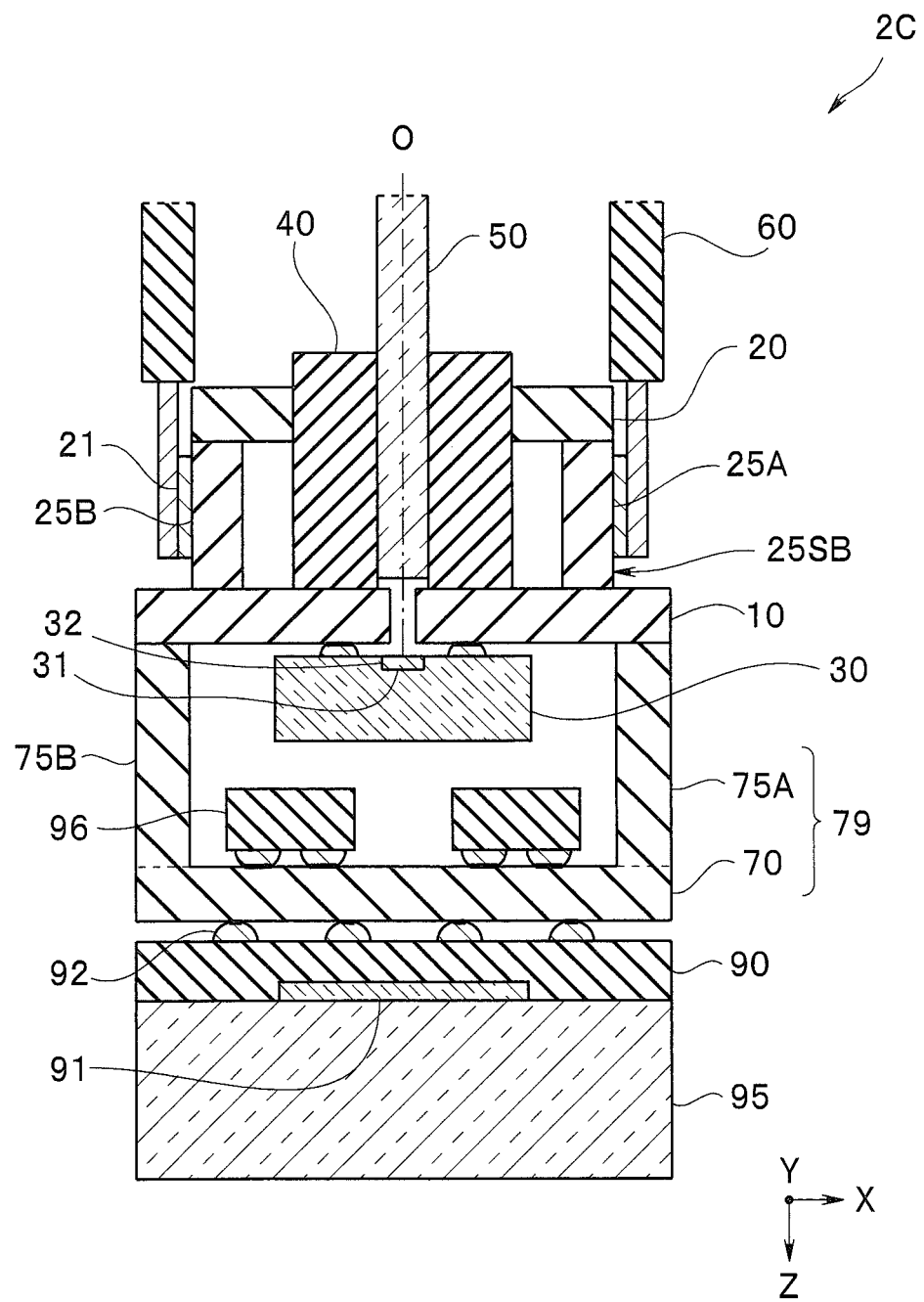
FIG. 14 is a sectional view of an image pickup module in a modification 3 of the second embodiment.

As shown in FIG. 14, in the image pickup module 2C in a modification 3 of the second embodiment, a side surface substrate has a function of an interconnecting substrate. In other words, the side surface substrate 25 (25A or 25B) connects the first substrate 10 and the holding substrate 20. The electrode 21 is disposed on the sixth principal plane 25SB, which is the outer surface of the side surface substrate 25.

The image pickup module 2C is shorter and smaller than the image pickup module 2 and the like.

Modification 4 of the Second Embodiment

Figure 15:
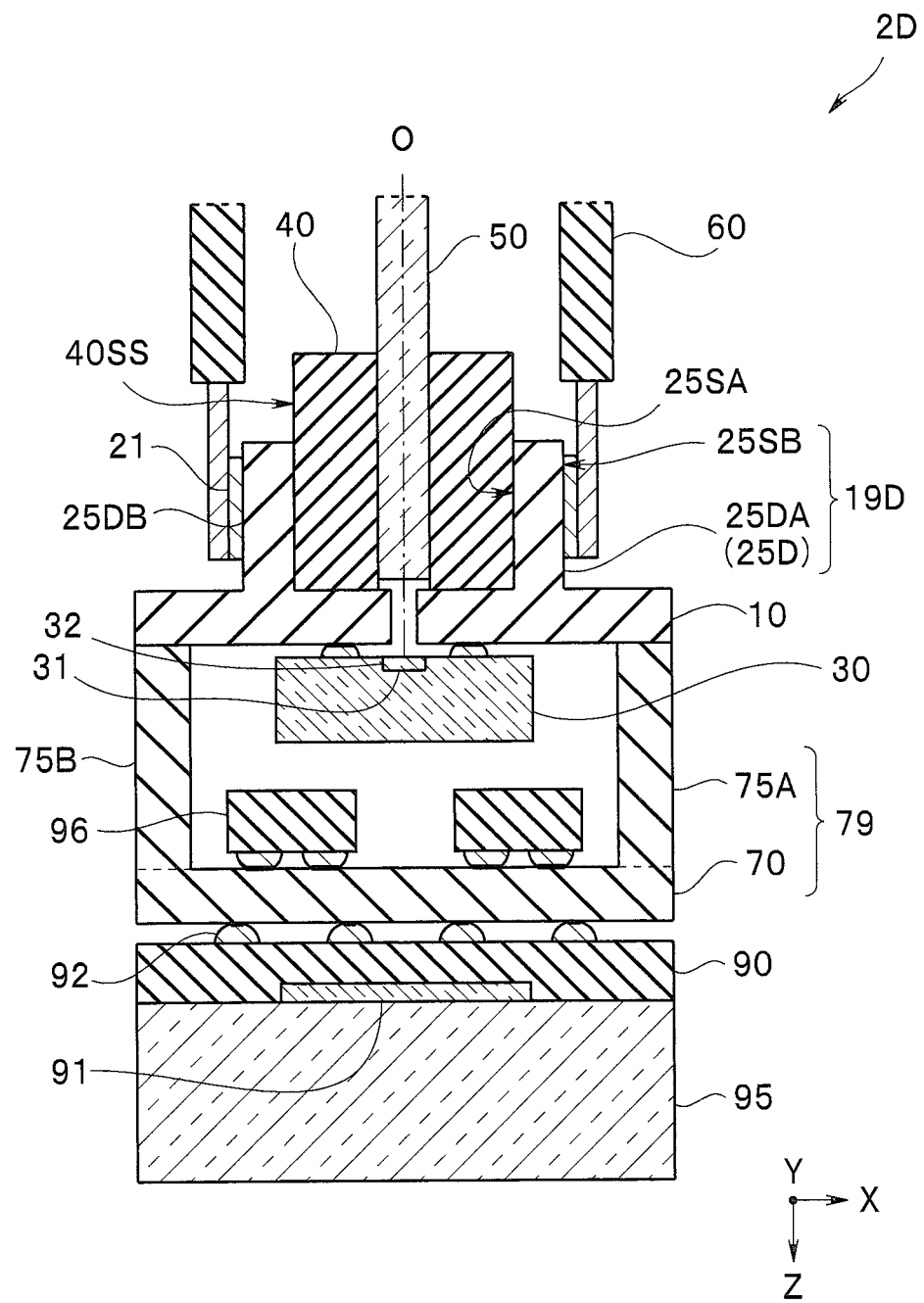
FIG. 15 is a sectional view of an image pickup module in a modification 4 of the second embodiment.

As shown in FIG. 15, in the image pickup module 2D in a modification 4 of the second embodiment, a side surface substrate 25D has a function of a holding substrate. In other words, the outer peripheral surfaces 40SS of the ferrule 40 are in contact with the fifth principal planes 25SA, which are the inner surfaces of side surface substrates 25DA and 25DB disposed to be facing each other, whereby positioning and holding are performed. In other words, the fifth principal plane 25SA of the side surface substrate 25D has a function of a wall surface of an opening of the holding substrate.

Note that the first substrate 10 and the side surface substrate 25D are an integral three-dimensional wiring board 19D.

As explained above, in the image pickup module 2D, the side surface substrate 25D has the function of the interconnecting substrate. The electrode 21 is disposed on the sixth principal plane 25SB. The plurality of side surface substrates 25D disposed in rotational symmetrical positions have the function of the holding substrate. The fifth principal planes 25SA of the plurality of side surface substrates 25D are in contact with the outer peripheral surface of the holding member.

The image pickup module 2D is shorter and smaller than the image pickup modules 2C and the like.

Third Embodiment

An endoscope 9 in a third embodiment includes the image pickup module 2 (or 2A to 2D) explained above.

Figure 16:
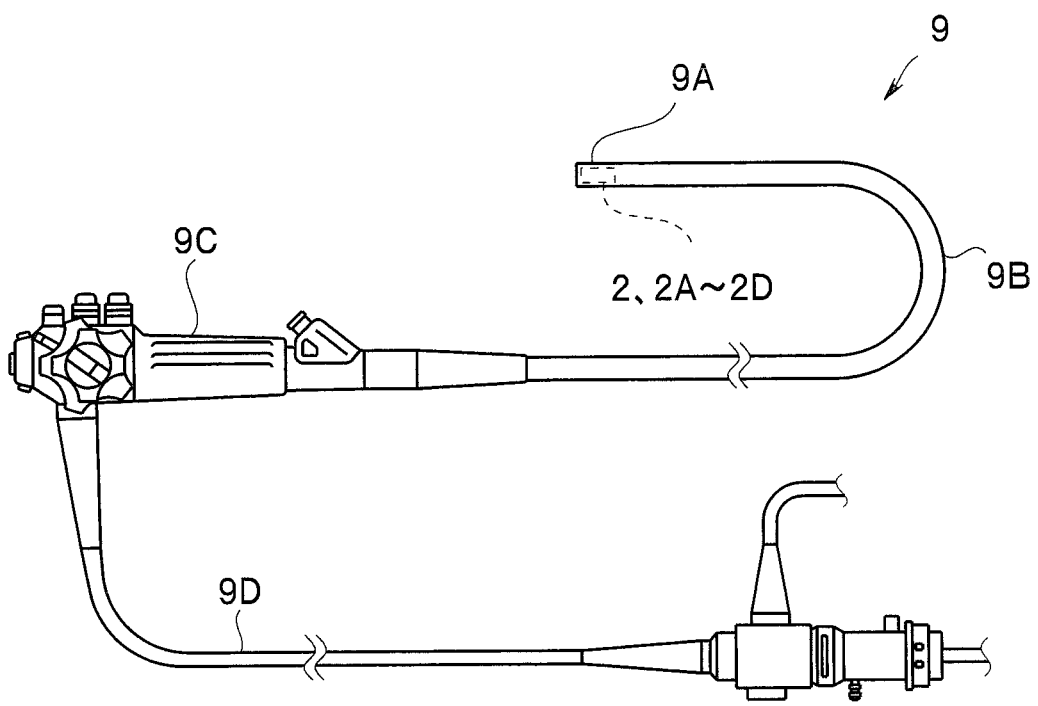
FIG. 16 is a perspective view of an endoscope in a third embodiment.

As shown in FIG. 16, the endoscope 9 includes an insertion section 9B in which the small-diameter and short and small image pickup module 2 and the like are housed in a distal end portion 9A, an operation section 9C disposed on a proximal end side of the insertion section 9B, and a universal cord 9D extended from the operation section 9C. The universal cord 9D is connected to the signal cable 60 of the image pickup module.

The endoscope 9 includes, at the distal end portion 9A of the insertion section 9B, the image pickup module 2 that is small in diameter and short and small and has high transmission efficiency and high reliability. Therefore, the endoscope 9 is minimally invasive and has high reliability. Note that the endoscope 9 is a flexible endoscope but may be a rigid endoscope. The endoscope in the embodiment may be a medical endoscope or may be an industrial endoscope.

The present invention is not limited to the embodiments or the modifications explained above. Various changes, combinations, and applications are possible within a range not departing from the gist of the invention.

What is claimed is:
1. An optical module comprising:
  an optical element including a light source or a photo sensor;
  a first substrate including a first principal plane and a second principal plane facing the first principal plane, the optical element being mounted on the first principal plane;
  a holding body disposed on the second principal plane of the first substrate such that a center axis of a through hole coincides with an optical axis of the optical element;
  an optical fiber inserted into the through hole of the holding body;
  a holding substrate with an opening including a third principal plane and a fourth principal plane facing the third principal plane, the third principal plane being disposed in parallel to the second principal plane of the first substrate, a wall surface of the holding substrate being in contact with an outer peripheral surface of the holding body;
  an interconnecting substrate connecting the first substrate and the holding substrate;
  a side surface substrate including a fifth principal plane, which is an inner surface, and a sixth principal plane, which is an outer surface, facing the fifth principal plane, the fifth principal plane being disposed in parallel to the optical axis, an end portion of the side surface substrate being connected to the holding substrate, an electrode being disposed on at least one of the fifth principal plane and the sixth principal plane; and
  a signal cable, a distal end portion of which is bonded to the electrode of the side surface substrate;
  wherein the interconnecting substrate, the holding substrate, the side surface substrate, the optical element, the holding body, and the distal end portion of the signal cable are included in a first space formed by extending the first substrate in an optical axis direction of the optical element, and
  the electrode of the side surface substrate is included in a second space formed by extending the holding body in a direction orthogonal to the optical axis.

2. The optical module according to claim 1, wherein the opening is a second through hole that pierces through the holding substrate.

3. The optical module according to claim 1, wherein the opening is a cutout of the holding substrate.

4. The optical module according to claim 1, wherein the side surface substrate in plurality is disposed in facing positions or orthogonal positions to surround the holding body.

5. The optical module according to claim 4, wherein the optical module includes a resin member that fills a space in which the holding body is disposed, the space being surrounded by the plurality of side surface substrates.

6. The optical module according to claim 1, wherein at least the first substrate and the interconnecting substrate or the holding substrate and the side surface substrate are an integral three-dimensional substrate made of ceramic or MID.

7. The optical module according to claim 1, wherein the first substrate, the interconnecting substrate, the holding substrate, and the side surface substrate are an integral substrate, at least connecting sections of which are flexible.

8. An image pickup module comprising:
  an optical module;
  an image pickup device including an image sensor on a light receiving surface the image pickup device further having a rear surface facing the light receiving surface, the image sensor being configured to output an image pickup signal;

a second substrate including a seventh principal plane and an eighth principal plane facing the seventh principal plane, the image pickup device being mounted on the seventh principal plane; and a second interconnecting substrate connecting the second substrate and a first substrate, wherein the optical module includes:

an optical element including a light source or a photo sensor;

the first substrate including a first principal plane and a second principal plane facing the first principal plane, the optical element being mounted on the first principal plane;

a holding body disposed on the second principal plane of the first substrate such that a center axis of a through hole coincides with an optical axis of the optical element;

an optical fiber inserted into the through hole of the holding body;

a holding substrate with an opening including a third principal plane and a fourth principal plane facing the third principal plane, the third principal plane being disposed in parallel to the second principal plane of the first substrate, a wall surface of the holding substrate being in contact with an outer peripheral surface of the holding body;

an interconnecting substrate connecting the first substrate and the holding substrate;

a side surface substrate including a fifth principal plane, which is an inner surface, and a sixth principal plane, which is an outer surface, facing the fifth principal plane, the fifth principal plane being disposed in parallel to the optical axis, an end portion of the side surface substrate being connected to the holding substrate, an electrode being disposed on at least one of the fifth principal plane and the sixth principal plane; and a signal cable, a distal end portion of which is bonded to the electrode of the side surface substrate;

wherein the second substrate, the second interconnecting substrate, the first substrate, the interconnecting substrate, the holding substrate, the side surface substrate, the optical element, the holding body, and the distal end portion of the signal cable are included in a space formed by extending the image pickup device in an optical axis direction, and the electrode of the side surface substrate is included in a second space formed by extending the holding body in a direction orthogonal to the optical axis.

9. The image pickup module according to claim 8, wherein the second substrate and the second interconnecting substrate are an integral three-dimensional substrate made of ceramic or MID.

10. The image pickup module according to claim 8, wherein the second substrate, the second interconnecting substrate, the first substrate, the interconnecting substrate, the holding substrate, and the side surface substrate are an integral substrate, at least connecting sections of which are flexible.

11. The image pickup module according to claim 8, wherein the side surface substrate has a function of the interconnecting substrate, and the electrode is disposed on the sixth principal plane.

12. The image pickup module according to claim 11, wherein the side surface substrate in plurality disposed in facing positions or orthogonal positions to surround the holding body has a function of the holding substrate, and the fifth principal plane of each of the plurality of side surface substrates is in contact with an outer peripheral surface of the holding body.

13. An endoscope comprising an image pickup module, wherein the image pickup module includes:

an optical module;

an image pickup device including an image sensor on a light receiving surface the image pickup device further having a rear surface facing the light receiving surface, the image sensor being configured to output an image pickup signal;

a second substrate including a seventh principal plane and an eighth principal plane facing the seventh principal plane, the image pickup device being mounted on the seventh principal plane; and a second interconnecting substrate connecting the second substrate and a first substrate, the optical module includes:

an optical element including a light source or a photo sensor;

the first substrate including a first principal plane and a second principal plane facing the first principal plane, the optical element being mounted on the first principal plane;

a holding body disposed on the second principal plane of the first substrate such that a center axis of a through hole coincides with an optical axis of the optical element;

an optical fiber inserted into the through hole of the holding body;

a holding substrate with an opening including a third principal plane and a fourth principal plane facing the third principal plane, the third principal plane being disposed in parallel to the second principal plane of the first substrate, a wall surface of the holding substrate being in contact with an outer peripheral surface of the holding body;

an interconnecting substrate connecting the first substrate and the holding substrate;

a side surface substrate including a fifth principal plane, which is an inner surface, and a sixth principal plane, which is an outer surface, facing the fifth principal plane, the fifth principal plane being disposed in parallel to the optical axis, an end portion of the side surface substrate being connected to the holding substrate, an electrode being disposed on at least one of the fifth principal plane and the sixth principal plane; and a signal cable, a distal end portion of which is bonded to the electrode of the side surface substrate, the second substrate, the second interconnecting substrate, the first substrate, the interconnecting substrate, the holding substrate, the side surface substrate, the optical element, the holding body, and the distal end portion of the signal cable are included in a space formed by extending the image pickup device in an optical axis direction, and the electrode of the side surface substrate is included in a second space formed by extending the holding body in a direction orthogonal to the optical axis.

* * * * *